(12) United States Patent
Prakash et al.

(10) Patent No.: US 6,180,156 B1
(45) Date of Patent: Jan. 30, 2001

(54) ACID SALTS OF N-[N-(3,3-DIMETHYLBUTYL)-L-α-ASPARTYL]-L-PHENYLALANINE 1-METHYL ESTER

(75) Inventors: Indra Prakash, Hoffman Estates; Kurt L. Wachholder, Elgin, both of IL (US)

(73) Assignee: The NutraSweet Company, Chicago, IL (US)

( * ) Notice: Under 35 U.S.C. 154(b), the term of this patent shall be extended for 0 days.

(21) Appl. No.: 09/146,964

(22) Filed: Sep. 4, 1998

Related U.S. Application Data

(60) Provisional application No. 60/058,505, filed on Sep. 11, 1997.

(51) Int. Cl.[7] .................................................. A23L 1/236
(52) U.S. Cl. ............................... 426/548; 560/40; 560/41
(58) Field of Search ............................... 426/548; 560/40, 560/41

(56) References Cited

U.S. PATENT DOCUMENTS

| | | | |
|---|---|---|---|
| 4,029,701 | 6/1977 | Haas et al. | 426/548 |
| 4,031,258 | 6/1977 | Haas et al. | 426/548 |
| 4,153,737 | 5/1979 | Berg et al. | 426/548 |
| 4,448,716 | 5/1984 | Tsau | 260/112.5 |
| 5,480,668 | 1/1996 | Nofre et al. | 426/548 |
| 5,510,508 | 4/1996 | Claude et al. | 560/41 |
| 5,728,862 | 3/1998 | Prakash | 560/40 |

FOREIGN PATENT DOCUMENTS

07680141A1    4/1997   (EP).

OTHER PUBLICATIONS

Benedetti, E. et al., "The Structure of New Dipeptide Taste Ligands", American Peptide Symposium, Nashville, TN, (Jun. 1997) P233 p. 2–127.

*Primary Examiner*—Leslie Wong
(74) *Attorney, Agent, or Firm*—Fitzpatrick, Cella, Harper & Scinto

(57) ABSTRACT

Dipeptide sweeteners are disclosed that are salts of N-[N-(3,3-dimethylbutyl)-L-α-aspartyl]-L-phenylalanine 1-methyl ester represented by the formula

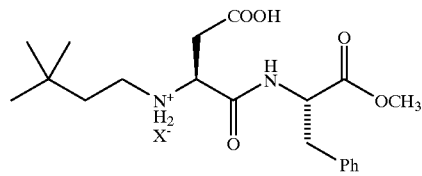

wherein $X^-$ is selected from the group consisting of $Cl^-$, $HSO_4^-$, $H_2PO_3^-$, citrate, $HCO_3^-$, furmarate, malate, maleiate, tartarate, acetate, benzoate or gluconate. Also disclosed is a liquid low-calorie sweetener containing such salts.

15 Claims, 1 Drawing Sheet

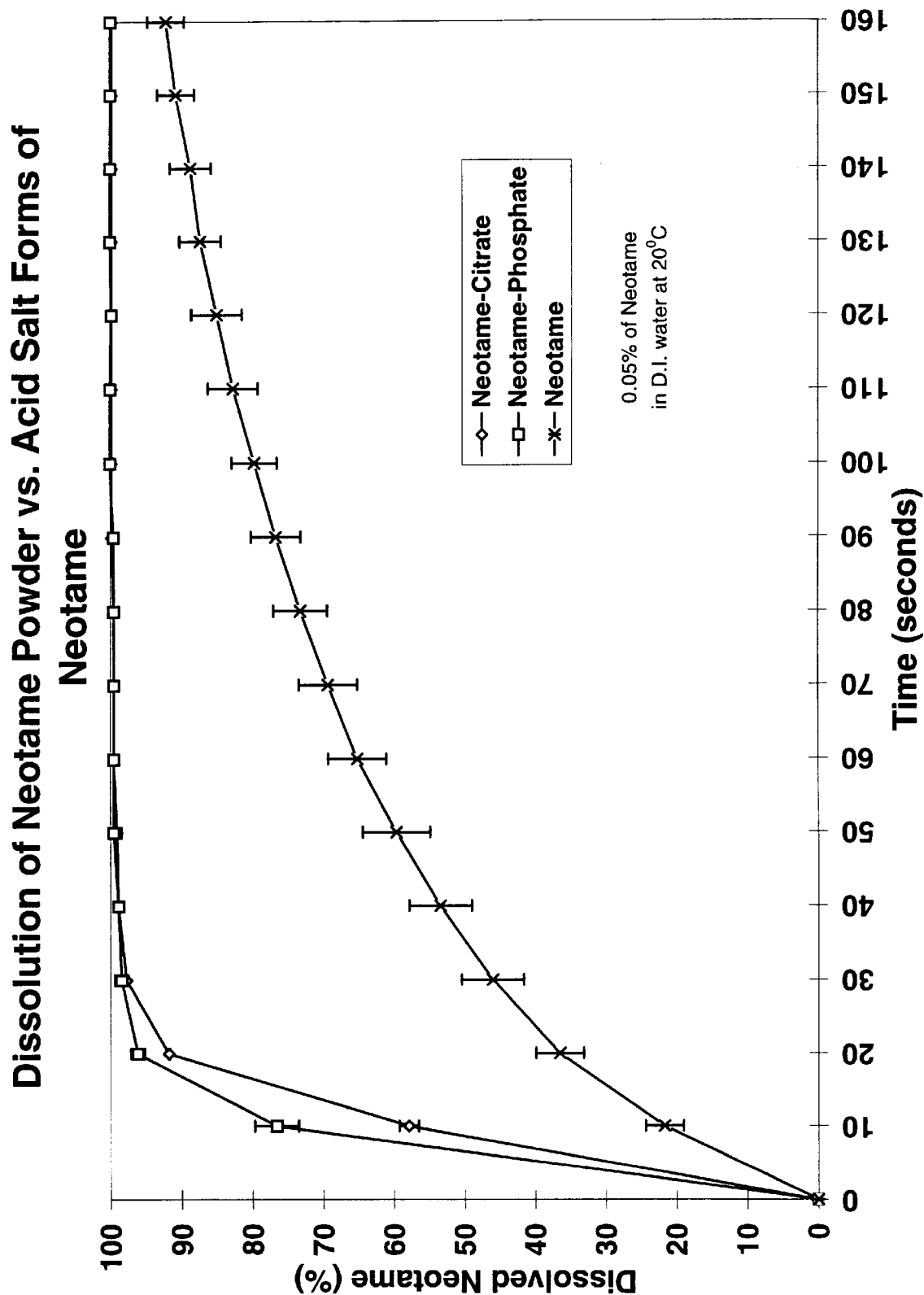

ACID SALTS OF N-[N-(3,3-DIMETHYLBUTYL)-L-α-ASPARTYL]-L-PHENYLALANINE 1-METHYL ESTER

This invention claims the benefit of U.S. Provisional Application Ser. No. 60/058,505, filed September 11, 1997.

BACKGROUND OF THE INVENTION

1. Field of the Invention

This invention relates to novel sweeteners. In particular, the invention relates to acid salts of the N-alkylated aspartame derivative, N-[N-(3,3-di-methylbutyl)-L-α-aspartyl]-L-phenylalanine 1-methyl ester, i.e., neotame. The invention also relates to a liquid low calorie sweetener containing such salts.

2. Related Background Art

It is known that various N-substituted derivatives of aspartame, such as disclosed in U.S. Pat. No. 5,480,668, are useful as sweetening agents. In particular, the N-alkylated aspartame derivative, N-[N-(3,3-dimethylbutyl)-L-α-aspartyl]-L-phenylalanine 1-methyl ester, is known as an extremely potent sweetening agent since its sweetening potency, on a weight basis, has been reported to be at least 50 times that of aspartame and about 10,000 times that of sucrose.

Since sweetening agents are often employed in aqueous solutions and beverages, it is important that they have an acceptable dissolution rate and an effective level of solubility to be commercially practicable. U.S. Pat. Nos. 4,029,701 and 4,031,258 describe inorganic salts of dipeptides that provide improved solubility in aqueous solution while maintaining the sweet property of the dipeptide. U.S. Pat. No. 4,448,716 describes certain dipeptide sweetener-metal complexes that provide improved dissolution and solubility. U.S. Pat. No. 4,153,737 describes concentrated solutions of dipeptide salts in a non-aqueous system (concentrated liquid low calorie sweetener). N-[N-(3,3-dimethyl-butyl)-L-α-aspartyl]-L-phenylalanine 1-methyl ester, however, is not disclosed or suggested.

Structurally, N-[N-(3,3-dimethylbutyl)-L-α-aspartyl]-L-phenylalanine 1-methyl ester and aspartame differ in that, in N-[N-(3,3-dimethylbutyl)-L-α-aspartyl]-L-phenylalanine 1-methyl ester, a bulky neohexyl substituent is present on the amine nitrogen.

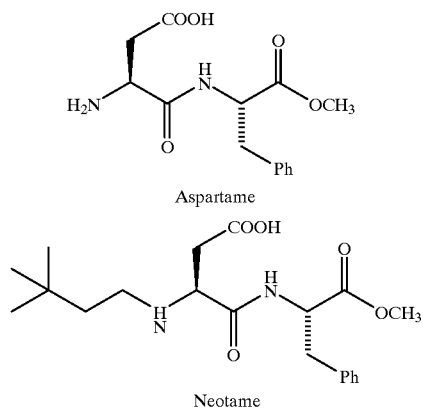

This structural difference results in dramatic differences in the physical and chemical properties of these compounds. For example, the melting point of N-[N-(3,3-dimethylbutyl)-L-α-aspartyl]-L-phenylalanine 1-methyl ester is 80° C., while that of aspartame is 248° C. In addition, N-[N-(3,3-dimethylbutyl)-L-α-aspartyl]-L-phenylalanine 1-methyl ester has much higher solubility in organic solvents than aspartame, and a much lower solubility in water. It is also known that N-[N-(3,3-dimethylbutyl)-L-α-aspartyl]-L-phenylalanine 1-methyl ester has a higher stability than aspartame under some pH conditions, as described in U.S. Pat. No. 5,480,688. The pronounced difference in sweetness between the two compounds is further evidence of their chemical dissimilarity.

Moreover, it is also known that a primary amino group such as the one on aspartame (pKa 7.7) generally has a different pKa than those from a secondary amino group such as the one on N-[N-(3,3-dimethylbutyl)-L-α-aspartyl]-L-phenylalanine 1-methyl ester (pKa 8.1). Moreover, the pKa's of an amino acid are known to have a profound impact on food applications (Labuza, T. P. and Basisier, M. W., 1992, "Physical Chemistry of Foods", H. G. Schwartzber and R. W. Hartel (Eds.), Marcel Dekker, Inc., New York). It is also well known that a secondary amine group can not form Schiff base type compounds with carbonyl compounds while a primary amine may. Furthermore, N-[N-(3,3-dimethylbutyl)-L-α-aspartyl]-L-phenylalanine 1-methyl ester exhibits physiologically different behavior than aspartame as exemplified by the dramatic difference in sweetness. These differences are clearly indicative that the characteristics and properties of one can not be said to suggest those of the other.

While N-[N-(3,3-dimethylbutyl)-L-α-aspartyl]-L-phenylalanine 1-methyl ester is a highly potent sweetener, it is sparingly soluble in water and can give rise to dusting problems. Therefore, there is a need for N-[N-(3,3-dimethylbutyl)-L-α-aspartyl]-L-phenylalanine 1-methyl ester derivatives that have good dissolution and solubility properties in aqueous systems, and avoid dusting problems often encountered with fine powders.

SUMMARY OF THE INVENTION

This invention relates to dipeptide sweeteners that are salts of N-[N-(3,3-dimethylbutyl)-L-α-aspartyl]-L-phenylalanine 1-methyl ester possessing good dissolution and solubility properties in aqueous systems. In particular, the salts of N-[N-(3,3-dimethylbutyl)-L-α-aspartyl]-L-phenylalanine 1-methyl ester of this invention are represented by the formula

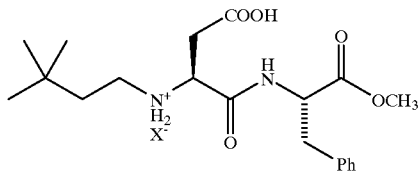

wherein X⁻ is selected from the group consisting of Cl⁻, $HSO_4^-$, $H_2PO_3^-$, citrate, $HCO_3^-$, furmarate, malate, maleiate, tartarate, acetate, benzoate or gluconate. The invention is also related to a liquid low calorie sweetener containing the acid salts of this invention.

BRIEF DESCRIPTION OF THE DRAWING

The FIGURE is a graph comparing the aqueous dissolution of N-[N-(3,3-dimethylbutyl)-L-α-aspartyl]-L-phenylalanine 1-methyl ester at a target concentration of 0.05% by weight with equivalent neotame concentrations, i.e., the concentration of the neotame delivered in each case is the same, of the phosphate and citrate salts of N-[N-(3,3-dimethylbutyl)-L-α-aspartyl]-L-phenylalanine 1-methyl ester.

DETAILED DESCRIPTION OF THE INVENTION

This invention is directed to salts of N-[N-(3,3-dimethylbutyl)-L-α-aspartyl]-L-phenylalanine 1-methyl ester, i.e., salts of neotame. U.S. Pat. No. 5,480,668, U.S. Pat. No. 5,510,508 and U.S. Pat. No. 5,728,862, which describe the preparation of N-[N-(3,3-dimethylbutyl)-L-α-aspartyl]-L-phenylalanine 1-methyl ester are incorporated by reference herein as if fully set forth. Thus, the starting material may be readily prepared by one of ordinary skill in the art without undue experimentation.

The acid salts of this invention may be prepared by first slurrying the N-[N-(3,3-dimethylbutyl)-L-α-aspartyl]-L-phenylalanine 1-methyl ester in a solvent or mixture of solvents. Exemplary solvents may include water, methanol, acetone, tetrahydrofuran and the like. The slurry is stirred and an equimolar amount of the desired acid is slowly added to dissolve the N-[N-(3,3-dimethylbutyl)-L-α-aspartyl]-L-phenylalanine 1-methyl ester and form the salt of this invention. The salt may be recovered by evaporation of the solvent, freeze drying or spray drying the resulting solution. The order of the addition of sweetener to acid has not been found to be of consequence and can be readily determined by those skilled in the art. Acid salts of N-[N-(3,3-dimethylbutyl)-L-α-aspartyl]-L-phenylalanine 1-methyl ester prepared under these conditions do not show any racemization. Addition of excess of acid (more than 1 equivalent) does cause hydrolysis of the methyl ester.

The acids employed in the preparation of the salts of this invention are typically selected from compounds that have a pKa effectively lower than the pKa of the secondary amine of N-[N-(3,3-dimethylbutyl)-L-α-aspartyl]-L-phenylalanine 1-methyl ester to result in the formation of the desired salt. Such compounds include, for example, hydrochloric acid, sulfuric acid, phosphoric acid, citric acid, fumaric acid, malic acid, maleic acid, tartaric acid, acetic acid, benzoic acid, gluconic acid and carbonic acid. As such, $X^-$ is a physiologically acceptable anion selected from the group consisting of $Cl^-$, $HSO_4^-$, $H_2PO_3^-$, citrate$^-$, $HCO_3^-$, furmarate, malate, maleiate, tartarate, acetate, benzoate or gluconate. These ions can be used alone or in combination.

Particularly preferred salts of this invention include the hydrochloride, phosphate, sulfate, citrate, hydrobromide and carbonic salts of N-[N-(3,3-dimethylbutyl)-1-L-α-aspartyl]-L-phenylalanine 1-methyl ester.

It is believed that the acid salts of this invention provide a number of improved properties over those of N-[N-(3,3-dimethylbutyl)-L-α-aspartyl]-L-phenylalanine 1-methyl ester. In particular, the aqueous solubility is increased and the dissolution rate of the composition is greatly improved. These acidic salts of neotame are sweet and it is also believed that these salts have improved taste. Thus, these salts of N-[N-(3,3-dimethylbutyl)-L-α-aspartyl]-L-phenylalanine 1-methyl ester will be particularly useful in beverage systems, particularly since additional methods or mechanical preparations are diminished or not necessary to provide for quick dissolution such as desired in a table top sweetener. The salts of this invention may be admixed with known bulking agents to prepare tablets, powdered or granular sweetener using methods well known to those skilled in the art.

These salts may also be used to prepare a liquid, low-calorie sweetener by dissolving a high concentration of the salt of this invention in an aqueous or alcoholic system, e.g., water, ethanol, water/ethanol, propylene glycol or propylene glycol/water. Such a liquid, low-calorie sweetener may find utility in such foodstuffs as gelatin desserts, fruit flavored beverages, cereal, cake mixes, fruit juices, syrups, salad dressings, pet foods, carbonated soft drinks, table top sweeteners and the like. Such utilities are not restrictive since other applications may include cough medicines, tonics and the like. One embodiment of this invention of particular interest contemplates a liquid table top sweetener as a replacement for sucrose and other known sweeteners. The liquid low calorie sweetener generally will contain up to about 40% by weight of the salt of N-[N-(3,3-dimethylbutyl)-L-α-aspartyl]-L-phenylalanine 1-methyl ester, the concentration depending of course on the desired end use.

The Examples which follow are intended as an illustration of certain preferred embodiments of the invention, and no limitation of the invention is implied.

EXAMPLE 1

Hydrochloride Salt of N-[N-(3,3-dimethylbutyl)-L-α-aspartyl]-L-phenylalanine 1-methyl Ester N-[N-(3,3-dimethylbutyl)-L-α-aspartyl]-L-phenylalanine 1-methyl ester (25.0 g) was slurried in 150 ml of water. To the stirred slurry was slowly added concentrated hydrochloric acid (5.5 ml, 0.0661 mol). After approximately 10 minutes all the solid had dissolved. The clear solution was then freeze dried. The resulting product exhibited a greatly increased aqueous solubility compared to the starting material. Yield: 27.34 g white solid (99.7%). The hydrochloride salt (1 g) dissolved in water (100 ml) in 70 seconds. 1H NMR ($CD_3CN$) δ 0.89 (s, 9H), 1.64 (m, 2H), 3.01 (m, 6H), 3.68 (s, 3H), 4.16 (t, 1H), 4.67 (m, 1H), 7.26 (m, 5H), 8.27 (d, 1H). Anal. Calcd for $C_{20}H_{31}ClN_2O_5 \cdot H_2O$: C, 55.48; H, 7.69; N, 6.47; Cl, 8.19. Found: C, 55.95; H, 7.59; N, 6.55; Cl, 8.35.

EXAMPLE 2

Phosphate Salt of N-[N-(3,3-dimethylbutyl)-L-α-aspartyl]-L-phenylalanine 1-methyl Ester N-[N-(3,3-dimethylbutyl)-L-α-aspartyl]-L-phenylalanine 1-methyl ester (10.0 g) was slurried in 100 ml of water. An equimolar amount of 85% phosphoric acid solution was added. After all the solid dissolved, the solution was freeze dried. The resulting product exhibited a greatly increased aqueous solubility compared to the starting material. Yield 12.33 g white solid (98.0%). The phosphate salt (0.1 g) dissolved in water (100 ml) in less than 30 seconds (visual observation) and about 90 seconds by spectrophotometric analysis. 1H NMR ($CD_3CN$) δ 0.89 (s, 9H), 1.55 (m, 2H), 2.84 (m, 5H), 3.19 (m, 1H), 3.67 (s, 3H), 4.06 (t, 1H), 4.70 (m, 1H), 7.27 (m, 5H), 8.03 (d, 1H). Anal. Calcd for $C_{20}H_{33}N_2O_9P \cdot H_2O$: C, 48.58; H, 7.15; N, 5.67; P, 6.26. Found: C, 48.15: H, 7.08; N, 5.60; P, 6.57.

EXAMPLE 3

Sulfate Salt of N-[N-(3,3-dimethylbutyl)-L-α-aspartyl]-L-phenylalanine 1-methyl Ester N-[N-(3,3-dimethylbutyl)-L-α-aspartyl]-L-phenylalanine 1-methyl ester (25.0 g) was slurried in 100 ml of water and concentrated sulfuric acid (3.67 ml) was added slowly. After several minutes of stirring some material remained undissolved. Therefore, 75 ml of acetone was added. The resulting clear solution was stirred for 30 minutes, then the acetone was removed under reduced pressure on a rotary evaporator. The contents of the flask remained a clear solution. Freeze drying of this solution afforded a white solid which exhibits a greater aqueous solubility compared to the starting material. Yield: 30.04 g (95%). The sulfate salt (0.1 g) dissolved in water (100 ml) in less than 20 seconds (visual observation). 1H NMR (CD$_3$CN) δ 0.89 (s,9H), 1.57 (m, 2H), 2.91 (m, 5H), 3.20 (m, 1H), 3.68 (s, 3H), 4.15 (t, 1H), 4.72 (m, 1H), 7.27 (m, 5H), 7.68 (d, 1H). Anal. Calcd for C$_{20}$H$_{32}$N$_2$O$_9$S.H$_2$O: C, 48.56; H, 6.94; N, 5.66; S, 6.48. Found C, 48.93; H, 7.02; N, 5.78; S, 6.50.

EXAMPLE 4

Citrate Salt of N-[N-(3,3-dimethylbutyl)-L-α-aspartyl]-L-phenylalanine 1-methyl Ester N-[N-(3,3-dimethylbutyl)-L-α-aspartyl]-L-phenylalanine 1-methyl ester (5.00 g) was dissolved in 75 ml of acetone. Citric acid (2.53 g) was dissolved in 50 ml of water, and the acetone solution was added. This formed a clear, colorless solution that was stirred for 1 hour. The acetone was evaporated under reduced pressure. The resulting slurry was freeze dried to obtain 7.5 g of a white solid. The citrate salt (0.1 g) dissolved in water (100 ml) in 90 seconds (visual observation). δ (CD$_3$CN) 0.89 (s, 9H), 1.53 (m, 2H), 2.83 (m, 10H), 3.20 (m, 1H), 3.67 (s, 3H), 4.04 (t, 1H), 4.21 (m, 1H), 7.27 (m, 5H), 7.79 (d, 1H). Anal. Calcd for C$_{26}$H$_{38}$N$_2$O$_{12}$.H$_2$O: C, 53.05; H, 6.86; N, 4.76. Found: C, 53.10; H, 6.88; N, 4.41.

COMPARATIVE EXAMPLE 1

Dissolution of N-[N-(3,3-dimethylbutyl)-L-α-aspartyl]-L-phenylalanine 1-methyl Ester in Water N-[N-(3,3-dimethylbutyl)-L-α-aspartyl]-L-phenylalanine 1-methyl ester (0.05–0.1 g) was dissolved in water (100 mL). The compound completely dissolved in 5–7 minutes (visual observation). The dissolution of 1.0 g of N-[N-(3,3-dimethylbutyl)-L-α-aspartyl]-L-phenylalanine 1-methyl ester in 100 mL of water required approximately 45 minutes.

Other variations and modifications of this invention will be obvious to those skilled in this art. This invention is not to be limited except as set forth in the following claims.

What is claimed is:
1. A salt of N-[N-(3,3-dimethylbutyl)-L-α-aspartyl]-L-phenylalanine 1-methyl ester represented by the formula

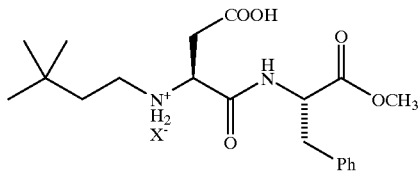

wherein X$^-$ is selected from the group consisting of Cl$^-$, HSO$_4^-$, H$_2$PO$_3^-$, citrate$^-$, HCO$_3^-$, furmarate, malate, maleiate, tartarate, acetate, benzoate or gluconate.
2. A salt according to claim 1, wherein X$^-$ is Cl$^-$.
3. A salt according to claim 1, wherein X$^-$ is HSO$_4^-$.
4. A salt according to claim 1, wherein X$^-$ is H$_2$PO$_3^-$.
5. A salt according to claim 1, wherein X$^-$ is citrate.
6. A salt according to claim 1, wherein X$^-$ is HCO$_3^-$.
7. A salt according to claim 1, wherein X$^-$ is furmarate.
8. A salt according to claim 1, wherein X$^-$ is malate.
9. A salt according to claim 1, wherein X$^-$ is maleiate.
10. A salt according to claim 1, wherein X$^-$ is tartarate.
11. A salt according to claim 1, wherein X$^-$ is acetate.
12. A salt according to claim 1, wherein X$^-$ is benzoate.
13. A salt according to claim 1, wherein X$^-$ is gluconate.
14. A liquid low-calorie sweetener composition comprising a salt of a dipeptide-sweetener represented by the formula

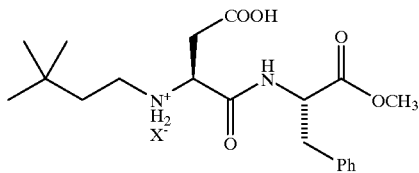

wherein X$^-$ is selected from the group consisting of Cl$^-$, HSO$_4^-$, H$_2$PO$_3^-$, citrate$^-$, HCO$_3^-$, furmarate, malate, maleiate, tartarate, acetate, benzoate or gluconate, dissolved in a consumable solvent or solvents in a concentration up to about 40% by weight of the composition to provide a high concentration liquid low-calorie sweetener.
15. A liquid low-calorie sweetener according to claim 14, wherein the solvent is ethanol, water, propylene glycol or a mixture thereof.

* * * * *

UNITED STATES PATENT AND TRADEMARK OFFICE
CERTIFICATE OF CORRECTION

PATENT NO. : 6,180,156 B1
DATED : January 30, 2001
INVENTOR(S) : Indra Prakash et al.

It is certified that error appears in the above-identified patent and that said Letters Patent is hereby corrected as shown below:

Column 3,
Line 43, "furmarate," should read -- fumarate, --.

Column 5,
Line 28, "δ (CD$_3$CN)" should read -- 1H NMR (CD$_3$CN) δ --.

Column 6,
Line 13, "furmarate," should read -- fumarate, --
Line 16, "X⁻is" should read -- X⁻ is --;
Line 23, "X⁻is" should read -- X⁻ is --; and
Line 40, "furmarate," should read -- fumarate, --.

Signed and Sealed this

Fourteenth Day of January, 2003

JAMES E. ROGAN
*Director of the United States Patent and Trademark Office*